(12) United States Patent
MacDonald et al.

(10) Patent No.: US 8,518,375 B2
(45) Date of Patent: Aug. 27, 2013

(54) ANTI-VIRAL TISSUE PRODUCT WITH VISUAL EFFICACY INDICATOR

(75) Inventors: John Gavin MacDonald, Decatur, GA (US); Stephanie M. Martin, Johns Creek, GA (US); Ronnie L. Phillips, Atlanta, GA (US); Xuedong Song, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 200 days.

(21) Appl. No.: 12/826,017

(22) Filed: Jun. 29, 2010

(65) Prior Publication Data

US 2011/0158917 A1 Jun. 30, 2011

Related U.S. Application Data

(63) Continuation-in-part of application No. 12/655,478, filed on Dec. 31, 2009.

(51) Int. Cl.
*A61K 31/194* (2006.01)
*A61K 9/70* (2006.01)
*A61P 31/12* (2006.01)

(52) U.S. Cl.
USPC .......................... 424/10.3; 424/405

(58) Field of Classification Search
USPC ................................ 424/10.3, 405
See application file for complete search history.

(56) References Cited

U.S. PATENT DOCUMENTS

| | | | | |
|---|---|---|---|---|
| H1967 H | * | 6/2001 | Woolf | 427/288 |
| 2008/0223413 A1 | * | 9/2008 | Radford | 134/34 |

FOREIGN PATENT DOCUMENTS

| | | | |
|---|---|---|---|
| JP | 2006-095233 A | | 4/2006 |
| JP | 2006095233 A | * | 4/2006 |
| WO | WO 00/32164 A1 | | 6/2000 |
| WO | WO 01/00023 A1 | | 1/2001 |
| WO | WO 01/29315 A1 | | 4/2001 |
| WO | WO 2007/034855 A1 | | 3/2007 |

* cited by examiner

*Primary Examiner* — Fereydoun G Sajjadi
*Assistant Examiner* — Courtney Brown
(74) *Attorney, Agent, or Firm* — Michael J. Sullivan (57) ABSTRACT

Anti-viral tissues are provided with a pH indicator which can communicate to a tissue user by means of visual indicia, via color changes, that the tissue has active ingredients. Furthermore, the pH indicators can be used to illustrate neutralization of the pH of infected nasal discharge, which has a higher pH than healthy nasal discharge, giving the user a reason to believe that the product is working to deactivate virus.

6 Claims, 6 Drawing Sheets

ANTI-VIRAL TISSUE PRODUCT WITH VISUAL EFFICACY INDICATOR

RELATED APPLICATION

The present application is a continuation-in-part of U.S. patent application Ser. No. 12/655,478, as filed Dec. 31, 2009, the contents of which are incorporated herein, and claims benefit of priority therefrom.

FIELD OF INVENTION

The present invention pertains to an anti-viral tissue-based product that has an anti-viral component and a pH indicator. The color of the pH indicator in one or more tissue sheets can change when the tissues come into contact with mucus or mucosal discharge.

BACKGROUND OF THE INVENTION

Kimberly-Clark Global Sales, LLC currently markets a tissue product (Kleenex® Anti-Viral facial tissue) that inactivates viruses associated with the common cold. One of the active ingredients is citric acid. Although the product is effective, some consumers may be skeptical because there is no physical evidence that any viruses present in their nasal discharge have been inactivated. Therefore there is a need for an anti-viral tissue product which provides a visual indicator that the tissue is actually working when the user blows their nose into the tissue.

SUMMARY OF THE INVENTION

A cellulosic tissue-based material having an anti-viral component or formulation and a color-changing pH indicator is described. The pH indicator can convey to a user a visual signal of the presence and efficacy of the anti-viral component in the tissue. This pH indicator can be either incorporated in the batch of tissue pulp material as part of the tissue making process, or later applied topically by printing or spraying an ink medium containing the pH indicator on a surface of a tissue sheet.

BRIEF DESCRIPTION OF THE FIGURES

The patent or application file contains at least one photograph executed in color. Copies of this patent application publication with color photograph(s) will be provided by the Office upon request and payment of the necessary fee.

FIGS. 6A and 6B are color photographs of a tissue sheet with a pH indicator ink printed on a tissue sheet. Similar to the photos in FIGS. 5A and 5B, FIG. 6A is before insult, and FIG. 6B is after insult. The photo in FIG. 6B clear shows a color change from green to dark blue in the region of the tissue contacted with the mucus.

DETAILED DESCRIPTION OF THE INVENTION

The present invention describes a simple mechanism to visually communicate to a user the efficacy of anti-viral formulations on tissue products. An anti-viral tissue product (which can be a facial tissue, bath tissue, paper towel and the like) which contains a pH-sensitive dye (pH indicator), or mixtures thereof, can change either from a colorless state to a colored state or from one color to another (both situations referred to herein as a "color change") when in contact with the moisture associated with nasal mucosal discharge. In particular, the nasal discharge or mucus of a normal healthy individual will typically have a pH in a range from about 5.5 to about 6.5. On the other hand, the nasal mucus of an individual infected with a cold virus has been reported to have an elevated pH from about 7.2 to about 8.3. (See "Rapidly Released Allergens from Short Ragweed Pollen" by Dr. David G. Marsh et al., Publication No. 417, O'Neill Research Laboratories, Good Samaritan Hospital, Baltimore, Md., Vol. 67, No. 3, pp 206-216 (1981); "Nasal pH Measurement: a Reliable and Repeatable Parameter" by R. J. A. England, Clinical Otolaryngology and Allied Sciences, Vol. 24, Number 1, February 1999; and "Significance of the pH of Nasal Secretions In Situ" by N. D. Fabricant, Archives of Otolaryngology, Vol. 34, Number 1, July 1941.)

For anti-viral tissue products having an acidic active ingredient, such as citric acid, the pH response of the tissue product to a mucous insult can be different for healthy mucus versus infected mucus, thus creating several product design opportunities. For example, if the desire is to simply provide a visual indicia that there is an active ingredient present in the tissue, one or more pH-sensitive dyes can be selected to provide a color change that can be triggered by either healthy or infected mucus. If the desire is to provide a visual indicia that the user is either healthy or infected, the pH-sensitive dye can be selected to provide one color change (or no color change) in the presence of healthy mucus and a different color change in the presence of infected mucus. In addition, if the desire is to provide a visual indicia that the tissue product is actually working to deactivate infected mucus, the pH-sensitive dye can be selected to provide a color change when the product is contacted by infected mucus, which exhibits another color change again or reverts back to the previous color as the elevated pH of the infected mucus is lowered by the anti-viral acid component in the tissue. In a similar manner, alternative virus inactivation chemistries could prompt further design opportunities provided the chemistry was sufficiently different from the target pH of the mucus and that a pH indicator with a suitable range is selected.

Hence in one aspect, the invention resides in an anti-viral tissue product comprising one or more tissue sheets containing an anti-viral component and a pH indicator, wherein the color of the pH indicator in one or more of the tissue sheets changes when contacted with mucus.

In another aspect, the invention resides in an anti-viral tissue product comprising one or more tissue sheets containing an acidic anti-viral component and a pH indicator, wherein the color of the pH indicator in one or more of the tissue sheets changes when contacted with mucus having a pH of about 5 or greater, more specifically from about 5.5 to about 6.5.

In another aspect, the invention resides in an anti-viral tissue product comprising one or more tissue sheets containing an acidic anti-viral component and a pH indicator, wherein the color of the pH indicator in one or more of the tissue sheets changes when contacted with mucus having a pH of about 7 or greater, more specifically from about 7.2 to about 8.3.

In another aspect, the invention resides in an anti-viral tissue product comprising one or more tissue sheets containing an acidic anti-viral component and a pH indicator, wherein the color of the pH indicator in one or more of the tissue sheets changes from an initial color (which includes colorless) to a first color when contacted with mucus and changes to a second color or reverts to the initial color as the pH of the mucus is neutralized or lowered by the acidic anti-viral component. The timeframe for the color changes will be dependent upon the pH of the nasal mucus.

In another aspect, the invention resides in an anti-viral tissue product comprising two outer tissue sheets and one or more inner tissue sheets, wherein an inner sheet contains an acidic anti-viral component and the outer sheets contain a pH indicator, wherein the color of the pH indicator in the outer tissue sheets changes when contacted with mucus. In this embodiment, the pH indicator is advantageously selected to change color when the pH is about 7.2 or greater, so that the mucous insult on one side of the tissue product creates a color change. But by the time any moisture reaches the other side of the tissue by passing through the inner sheet(s) containing the acidic anti-viral composition, the mucus is neutralized so that the color change is not present on the opposite side of the tissue, indicating to the user that the tissue is working.

The acidic anti-viral component can be any composition containing an acid. Such compositions include, but are not limited to, acids having the formula R—COOH, where "R" is selected from the group consisting of lower alkyl, substituted lower alkyl, carboxy lower alkyl, carboxy hydroxyl lower alkyl, carboxy halo lower alkyl, carboxy dihydroxy lower alkyl, dicarboxy hydroxyl lower alkyl, lower alkenyl, carboxy lower alkenyl, dicarboxy lower alkenyl, and phenyl and substituted phenyl groups. "R" is preferably selected from the group consisting of carboxy hydroxy lower alkyl, carboxy dihydroxy lower alkyl, and dicarboxy hydroxy lower alkyl groups. Such compositions can also contain surfactants, particularly anionic surfactants. Particularly preferred compositions include citric acid, malic acid, mixtures of citric acid and malic acid, and combinations of those acids with sodium lauryl sulfate. Suitable acidic anti-viral components are disclosed in U.S. Pat. No. 4,738,847 entitled "Multi-Ply Virucidal Product" issued Apr. 19, 1988 to Rothe et al.; U.S. Pat. No. 4,828,912 entitled "Virucidal Product Having Virucidal and/or Germicidal Properties" issued May 9, 1989 to Hossain et al., both of which are hereby incorporated by reference in their entirety. Other compositions can be used provided they are safe and effective, including antiviral compositions that are not acidic and have pH values about 7 or greater. All that is required is that the presence of mucus in the tissue creates a pH change that can be detected by a suitable pH indicator.

The add-on amount of the acidic anti-viral component in the tissue (based on the dry weight of fiber in the tissue) can be from about 1 to about 15 dry weight percent, more specifically from about 5 to about 15 dry weight percent, and still more specifically from about 5 to about 10 dry weight percent. A particularly preferred acidic anti-viral component comprises about 7.5 dry weight percent citric acid and about 2 dry weight percent sodium lauryl sulfate.

The pH indicator can be any color changing dye that changes color in the pH range from about 5 to about 9 and is stable, non-bleeding and safe when incorporated into a tissue sheet. Such commercially available pH indicators include, but are not limited to, Alizarin (C.A.S. No. 72-48-0), Alizarin Yellow (C.A.S. No. 584-42-9), Alizarin Red S(C.A.S. No. 130-22-3), Basic Fushsin (C.A.S. No. 569-61-9), Brilliant Yellow (C.A.S. No. 3051-11-4), Bromochlorophenol Blue (C.A.S. No. 102185-52-4), Bromocresol Green (C.A.S. No. 76-60-8), Bromocresol Purple (C.A.S. No. 115-40-2), Bromophenol Blue (C.A.S. No. 115-39-9), Bromothymol Blue (C.A.S. No. 34722-90-2), Chlorophenol Red (C.A.S. No. 4430-20-0), Chrysoidin (C.A.S. No. 532-82-1), Congo Red (C.A.S. No. 573-58-0), o-Cresolphthalein (C.A.S. No. 596-27-0), Cresol Red (C.A.S. No. 1733-12-6), Ethyl Orange (C.A.S. No. 62758-12-7), m-Cresol Purple (C.A.S. No. 2303-01-7), Methyl Orange (C.A.S. No. 547-58-0), Methyl Red (C.A.S. No. 493-52-7), Mordant Orange I (C.A.S. No. 2243-76-7), Neutral Red (C.A.S. No. 553-24-2), Nile Blue A (C.A.S. No. 3625-57-8), Nitrazine Yellow (C.A.S. No. 5423-07-4), 3-Nitrophenol (C.A.S. No. 554-84-7), 4-Nitrophenol (C.A.S. No. 100-02-7), Phenolphthalein (C.A.S. No. 77-09-8, Phenol Red (C.A.S. No. 143-74-8), Rosolic Acid (C.A.S. No. 603-45-2), Thymol Blue (C.A.S. No. 76-61-9), Thymolphthalein (C.A.S. No. 125-20-2), and Xylenol Blue (C.A.S. No. 125-31-5. Additional suitable pH indicators or dyes are disclosed in U.S. Pat. No. 4,029,598 entitled "Non-Bleeding Indicator and Dyes Therefor", issued Jun. 14, 1977 to Neisius et al., which is hereby incorporated by reference. As disclosed therein, particularly suitable dyes include: 4-anilino-3"-azobenzene, which turns deep purple in the pH range of 0-4.5; 4-anilino-3'-azobenzene, which turns deep purple in the pH range of 0-3; and a 1:1:3 weight ratio of a mixture of 4-anilino-3-azobenzene, 2-(2,4-dinitrophenylazo)-4-napthol-sulphonic acid, and 4-methylamido-2-dimethylaminobenzene sulfonic acid, which turns from yellow to green in the pH range of 2-3.

The add-on amount of the pH indicator in the tissue (based on the dry weight of fiber in the tissue), can be from about 0.01 to about 10 dry weight percent, more specifically from about 0.1 to about 5 dry weight percent and still more specifically from about 0.01 to about 1 dry weight percent. The proper amount will depend, at least in part, upon the amount and strength of the acid component of the acidic anti-viral composition and the pH color change range of the chosen pH indicator.

The pH indicator, which can be water soluble or water insoluble, can be incorporated into the tissue sheet(s) by any suitable method, such as by topical addition via printing or spraying the pH indicator onto an existing tissue web or sheet. In such cases, the tissue sheet can be wet (after formation and prior to drying) or dry when the pH indicator is applied. Alternatively, the pH indicator can be incorporated into the fiber furnish prior to sheet formation. In one such embodiment, a pH indicator sheet, such as a conventional pH indicator strip or a larger sheet, can be provided and fiberized, wherein the resulting pH indicator-containing fibers can be combined with selected tissue making fibers prior to forming the tissue sheet. In another such embodiment, the pH indicator can be applied and bonded to papermaking fibers to produce pH indicator-containing fibers. These pH indicator-containing fibers can be provided as pulp sheets (wet or dry) or an aqueous pulp slurry that can be combined with select tissue making fibers prior to forming the tissue sheet in a conventional manner.

In all cases where the pH indicator is combined with papermaking fibers prior to tissue sheet formation, it is necessary that the pH indicators be adequately bonded to the cellulose fibers so that they are retained on the fibers when exposed to the aqueous environment associated with tissue forming and not lost in the process water. A high degree of retention can be attained by attaching appropriate groups to the dye molecules which covalently bond the dye molecules to the carrier (cellulose fibers). Such suitable non-bleeding dyes are disclosed in the aforementioned patent to Neisius et al., previously incorporated by reference.

The tissue product can comprise one, two, three or more tissue sheets or plies. The individual tissue sheets can be any tissue sheet suitable for use in facial tissues, bath tissues, paper towels and the like. Such sheets are well known in the art and include wet-laid tissue sheets, airlaid tissue sheets, wet-pressed tissue sheets, throughdried tissue sheets, creped tissue sheets, uncreped tissue sheets and the like. The tissue sheets will typically comprise cellulosic papermaking fibers, although some synthetic fibers can also be present. While the acidic anti-viral component and the pH indicator can be independently contained within any ply of a multi-ply tissue product, for some commercial applications it may be advantageous to combine the pH indicator with the acidic anti-viral component prior to incorporating the two components into the tissue sheet, such as incorporating all of the components into the center ply of a 3-ply tissue product. Alternatively, the center ply can be treated with the acidic anti-viral component and the outer plies can be independently treated with one or more pH indicators by any of the methods described above.

In the interests of brevity and conciseness, any ranges of values set forth in this specification contemplate all values within the range and are to be construed as written description support for claims reciting any sub-ranges having endpoints which are whole number or otherwise of like numerical values within the specified range in question. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5. Similarly, a disclosure in this specification of a range from 0.1 to 0.5 shall be considered to support claims to any of the following ranges: 0.1-0.5; 0.1-0.4; 0.1-0.3; 0.1-0.2; 0.2-0.5; 0.2-0.4; 0.2-0.3; 0.3-0.5; 0.3-0.4; and 0.4-0.5. In addition, any values prefaced by the word "about" are to be construed as written description support for the value itself. By way of example, a range of "from about 1 to about 5" is to be interpreted as also disclosing and providing support for a range of "from 1 to 5", "from 1 to about 5" and "from about 1 to 5".

According to another embodiment, in contrast to incorporating the color-indicators into the tissue pulp batch, as part of the tissue making process, one can apply the indicator as part of post tissue-making modifications to the tissue sheets. For instance, one can apply the indicator topically as an ink-based medium, which is printed on a surface of a tissue sheet. The pH indicator can be applied by means of a pH indicating ink.

The ink composition may include any combination of, but not limited to, a pH indicator, an ink base or carrier medium, a surfactant, an immobilizer, a pH adjuster, and solvent, in the following ranges: pH indicator 0.01-10 wt. %; ink carrier medium 20-95 wt. %; surfactant 0-25 wt. %; immobilizer 2-25 wt. %; pH adjuster 0-25 wt. %; and solvent 20-90 wt. %. Alternative ranges may include: about 1-3-6 wt. % or 8 wt. % pH indicator; about 30-45-90 wt. % or 93 wt. % ink carrier medium; about 0.5-5-10 wt. % or 15 wt. % surfactant; about 4-7-20 wt. % or 22 wt. % immobilizer; about 0.1-2-20 wt. % or 22 wt. % pH adjuster; and about 34-40-80 wt. % or 85 wt. % solvent.

A pH indicator and/or combination of different pH indicators can exhibit a clear color transition upon contact with nasal mucus and can be immobilized onto the substrate surface. The pH indicator or combination of pH indicators may include for example, but are necessarily not limited to: phloxine b, bromophenol blue, bromochlorophenol blue, bromocresol green, bromocresol purple, bromothymol blue, chlorophenol red, and nitrazine yellow. Various combinations of these indicators can be used according to the desired color manifestation.

The ink base or carrier medium has a formulation that helps make the pH indicator printable, and can be either a polar or non-polar organic solvent. Preferably the ink base is a polar soluble material, such as alcohol-based solvents. Examples of such ink bases can be but are not limited to Dermacryl, Amphomers, and Gantrez series as well as organic-based varnishes.

The surfactants, which enhance wettability of the ink can be any combination of cationic, anionic, or neutral surfactants. Examples of such surfactants include, but are not limited to, tween, sodium dodecyl sulfate, and cetyltrimethylammonium bromide. The immobilizer can be any combination of anionic or cationic agents such as benzethonium chloride, benzothonium chloride and cetyltrimethylammoniumchloride.

A buffering agent or pH adjuster can be any combination of weak acids. Examples of such pH adjusters may include oxalic acid, lactic acid, citric acid, malic acid, and polyacrylic acid. The solvent can be any combination of organic based solvent, especially, but not limited to, alcohol-based solvents. Examples of such solvents are ethanol, propanol, isopropanol, and methanol.

EXAMPLES

All chemicals described in the following Examples were purchased from Sigma-Aldrich (Milwaukee, Wis.) and used without further purification unless otherwise mentioned. The pH indicator strips were obtained from EMD Chemicals Inc. (Gibbstown N.J.).

Example 1

Confirming Nasal Mucus pH and Use of pH Indicator Dyes

Nasal discharge from healthy volunteers was collected using a regular Kleenex® facial tissue (Kimberly-Clark Corporation, Neenah Wis.). About 0.5 ml of the fluid was then transferred to the upper surface of a section of a Kleenex® Anti-Viral facial tissue (Kimberly-Clark Corporation, Neenah, Wis.) which was positioned on top of a ColorpHast® pH (4.0-7.0) strip (EMD Chemicals, Inc., Gibbstown, N.J.). The migration of the fluid down through the tissue sample caused the color of the indicator strip to change from yellow to greenish brown, indicating that the pH of normal nasal mucus is about 5.5-6.5 (according to the guide provided with the strips).

About 0.5 ml of a second amount of the nasal discharge was taken and spiked with about 0.1 ml of a pH 7.4 phosphate buffer. The spiked nasal discharge was then applied to a different section of the surface of the tissue sample having a new pH indicator strip placed below it. The fluid which migrated through the tissue sample contacted the new indicator strip and caused it to change from yellow to dark blue, indicating that mucus having a more basic pH than healthy mucus would register a different response with the pH indicator on the tissue.

Example 2

Testing Nasal Discharge from Volunteers Suffering with the Common Cold

Over a period of one month, twelve volunteers having the common cold were asked to blow their nose into a regular Kleenex® facial tissue and, using pH indicator strips (pH 0-14, EMD Chemicals Inc., Gibbstown, N.J.), estimate the pH of the nasal discharge. In all cases, the pH of the infected nasal mucus was found to be approximately pH 8. One volunteer continued to measure their nasal mucus once a day over a two week period to monitor when the nasal mucus returned to the healthy range (pH of 5.5-6.5). It was observed that the person felt that they had essentially recovered before the nasal pH had returned to the normal pH level.

Example 3

Tissue Preparation

Bromocresol Purple (Sigma-Aldrich, Cat. #860891), Bromothymol Blue (Sigma-Aldrich, Cat. # B8630). Chlorophenol Red (Sigma-Aldrich, Cat. #235482), and Cresol Red (Sigma-Aldrich, Cat. #114480) were identified as potential pH indicators for purposes of this invention due to their distinct color transitions between pH values of 5-9. Stock solutions of each indicator were prepared at 10 mg/ml in deionized water and diluted to 1 mg/ml in deionized water for the experiments described below. A summary of the indicator properties are listed in Table 1.

TABLE 1

(Summary of Investigated pH Indicators)

| pH Indicator | C.A.S. Number | pH Transition | Color Transition |
|---|---|---|---|
| Bromocresol Purple | 62625-30-3 | 5.2-6.8 | Yellow-Purple |
| Bromothymol Blue | 34722-90-2 | 6.0-7.6 | Yellow-Blue |
| Chlorophenol Red | 123333-64-2 | 4.8-6.4 | Yellow-Reddish Purple |
| Cresol Red | 62625-29-0 | 7.2-8.8 | Yellow-Reddish Purple |

Kleenex® Anti-Viral facial tissues, which are 3-ply tissue products containing an acidic anti-viral composition in the center ply (7.51 dry weight percent citric acid and 2.02 dry weight percent sodium lauryl sulfate), were used for the following experiments. The top outer ply or sheet of each 3-ply tissue was temporarily separated from the remaining two sheets. The top sheet of the remaining two sheets (originally the center ply of the 3-ply product) contained the acidic anti-viral formulation. Each selected pH indicator was sprayed directly onto the remaining top sheet using an aerosol spray (PALL Chromist™, Cat. # PN51901). The add-on amount was about 5 ml of 1 mg/ml indicator solution. The treated tissue sheets were allowed to dry overnight.

Figure 1A:
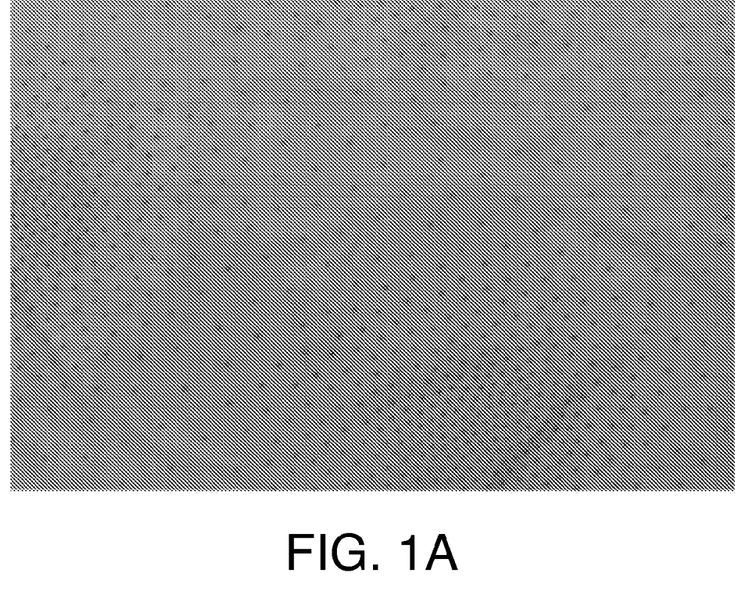
FIGS. 1A and 1B are color photographs of the surface of the center ply of a Kleenex® Anti-Viral facial tissue which has been spray-coated with a pH indicator in accordance with this invention. The tissue of FIG. 1A was sprayed with Bromothymol Blue and the tissue of FIG. 1B was sprayed with Cresol Red.
Figure 1B:
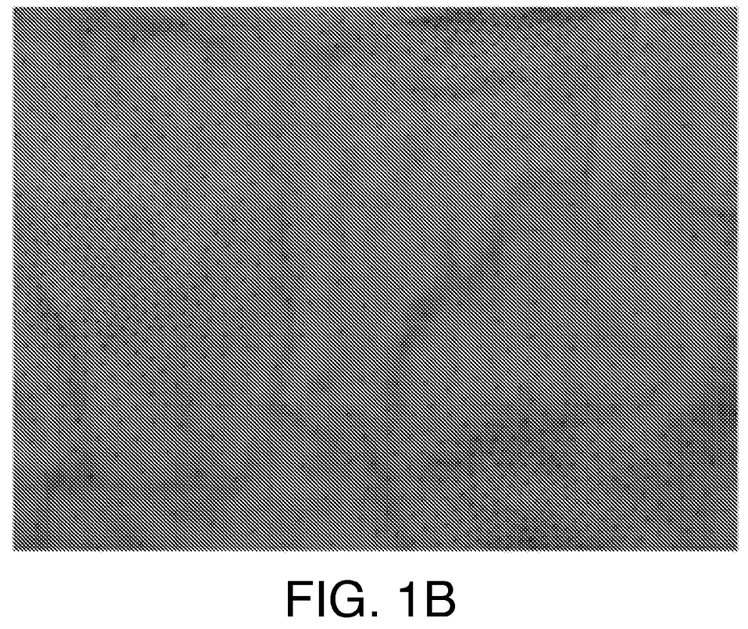

Once the tissues had dried, distinct differences in how the pH indicator coated the tissue were observed. For Bromothymol Blue (see FIG. 1A) and Chlorophenol Red, the indicator appeared as a uniform yellow color across the tissue, while the Bromocresol Purple and the Cresol Red (see FIG. 1B) appeared as a blotchy pattern across the center ply of the tissue due to lack of dye coating uniformity. Consequently, Bromothymol Blue and Chlorophenol Red were selected for further experiments. From the intense colors observed when the pH indicators were deposited onto the surface of the tissue samples, it is likely that the dye concentrations can be greatly reduced, such as about 0.01 mg/ml, and still exhibit a visual color change.

Example 4

Color Response Upon Treatment with Synthetic Nasal Mucus

The tissues of Example 3, which had been treated with Bromothymol Blue and Chlorophenol Red, were restored to their original 3-ply form by replacing the temporarily removed top outer ply. The resulting 3-ply tissues of this invention were subjected to both synthetic healthy nasal mucus and synthetic nasal mucus that mimicked a cold infection. Synthetic mucus was created according to the following protocol: Briefly, METHOCEL™ J12MS (Dow Chemical, Midland, Mich.) was dissolved in deionized water at ambient temperature at a concentration of 0.75% W/W while stirring rapidly. The pH was kept below 7.5 during this phase. After dispersion was completed, 0.1N NaOH was added drop wise until the pH was raised to >8.5. Rapid stirring was continued for approximately 30 minutes after the pH was increased until the solution was fully thickened and clear. For "healthy" nasal mucus, the pH was then adjusted using 0.1N HCl to a final pH of 5.5. For "sick" nasal mucus, the pH was adjusted to a final pH of approximately 8.0. Both indicators exhibited distinct color changes between healthy and infected mucus.

Figure 2A:
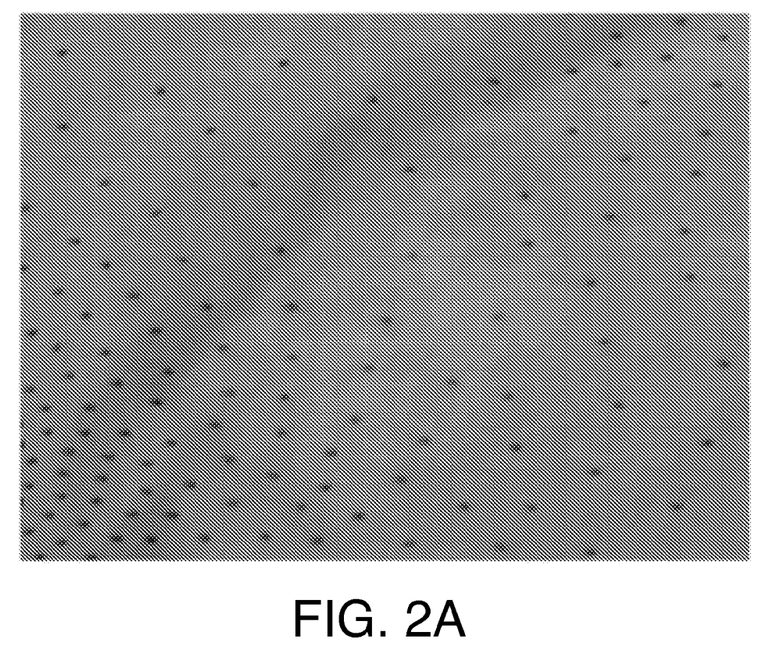
FIGS. 2A and 2B are color photographs of the surface of the center ply of a Kleenex® Anti-Viral facial tissue which has been spray-coated with Chlorophenol Red in accordance with this invention. The tissue of FIG. 2A was further treated with synthetic nasal mucus that mimicked healthy mucus, while the tissue of FIG. 2B was treated with synthetic nasal mucus that mimicked a cold infection.
Figure 2B:
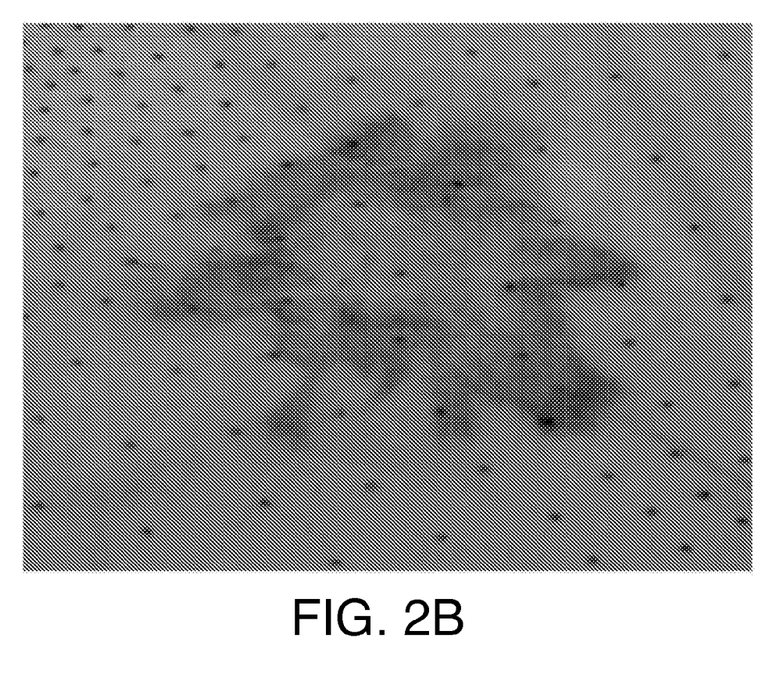

More specifically, with the Chlorophenol Red treated tissue, little to no color change was observed with normal synthetic mucus (see FIG. 2A), while the appearance of a reddish purple color appeared with infected synthetic mucus (see FIG. 2B). Also, as shown in FIG. 2B, the color begins to slowly de-colorize from the center of the spot outwards as the acid in the anti-viral formulation begins to neutralize the high pH of the infected synthetic mucous sample.

Figure 3A:
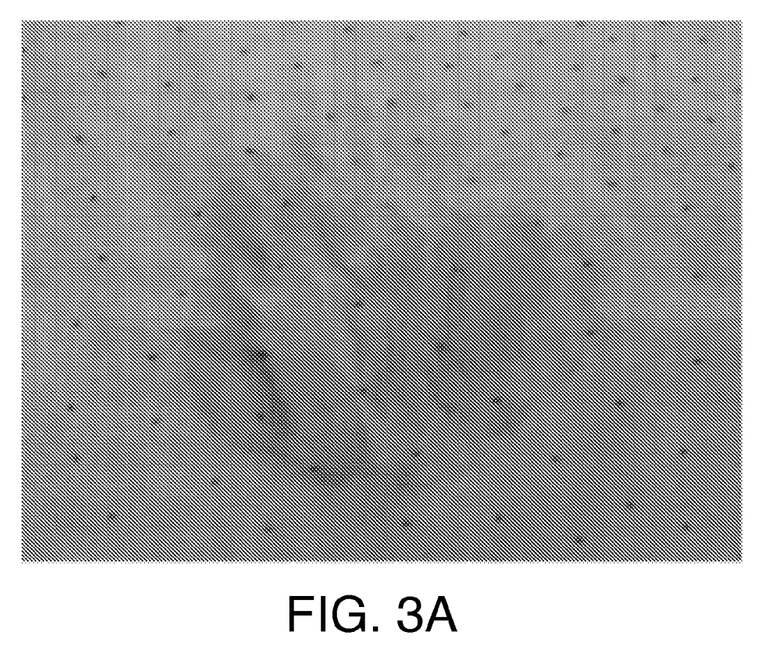
FIGS. 3A and 3B are color photographs of the surface of the center ply of a Kleenex® Anti-Viral facial tissue which has been spray-coated with Bromothymol Blue in accordance with this invention. The tissue of FIG. 3A was further treated with synthetic nasal mucus that mimicked healthy mucus, while the tissue of FIG. 3B was treated with synthetic nasal mucus that mimicked a cold infection.
Figure 3B:
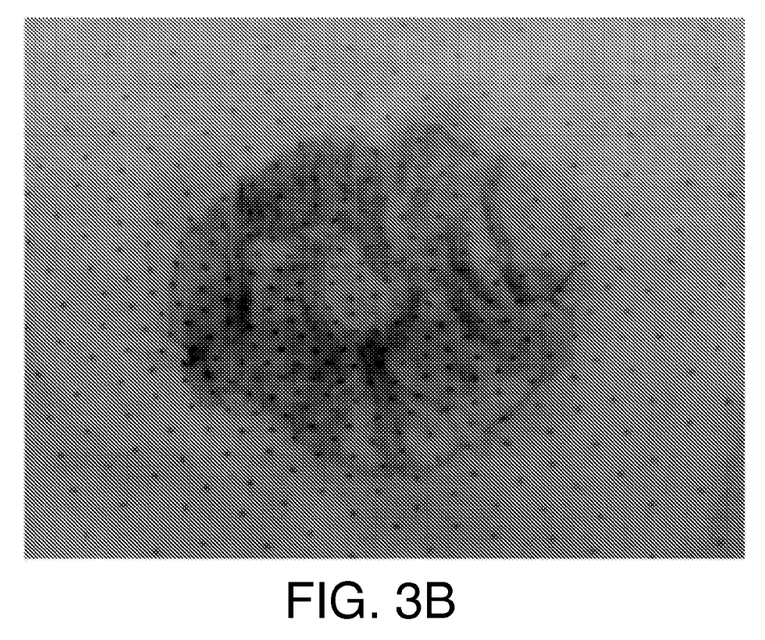
Figure 4A:
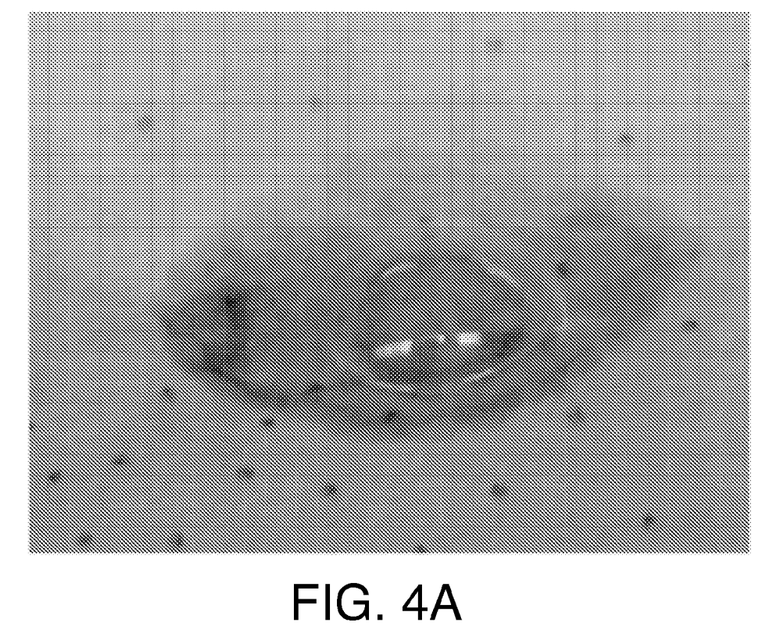
FIGS. 4A and 4B are color photographs of the surface of the center ply of a Kleenex® Anti-Viral facial tissue which has been spray-coated with Bromothymol Blue in accordance with this invention and thereafter treated with synthetic nasal mucus that mimicked a cold infection. The photograph of FIG. 4A was taken at 0 minutes and the photograph of FIG. 4B was taken at 5 minutes.
Figure 4B:
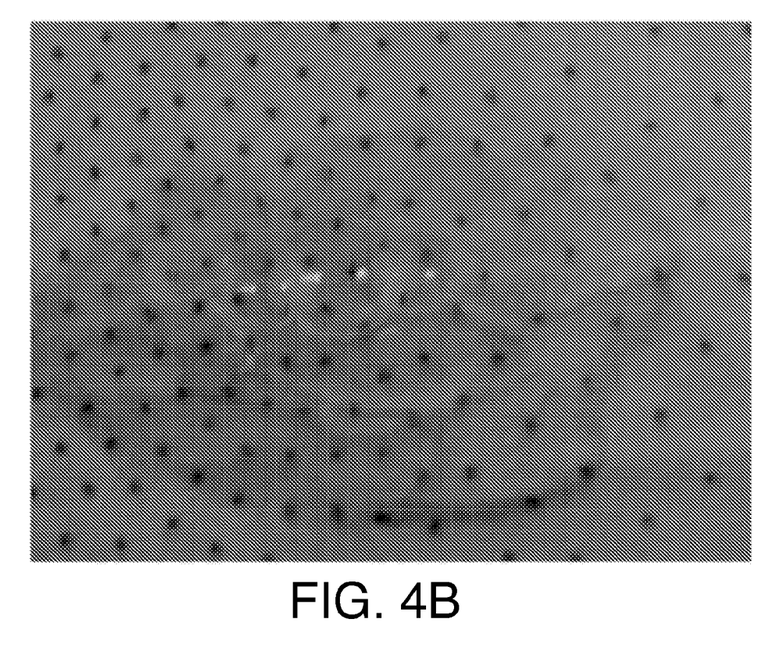

With the Bromothymol Blue treated tissue, little to no color change was observed with normal synthetic mucus (see FIG. 3A), while the appearance of a bright blue color appeared with infected synthetic mucus (see FIG. 3B). Also, as shown in FIG. 3B, the color begins to slowly de-colorize from the center of the spot outwards as the anti-viral formulation begins to neutralize the high pH of the infected synthetic mucous sample. However, due to the pH transition range of Bromothymol Blue, the color de-colorization occurs within a few minutes and the tissue returns to the original color (see FIGS. 4A and 4B).

Example 5

Tissue Sheet with Topically or Printed pH Indicator Ink

Figure 5A:
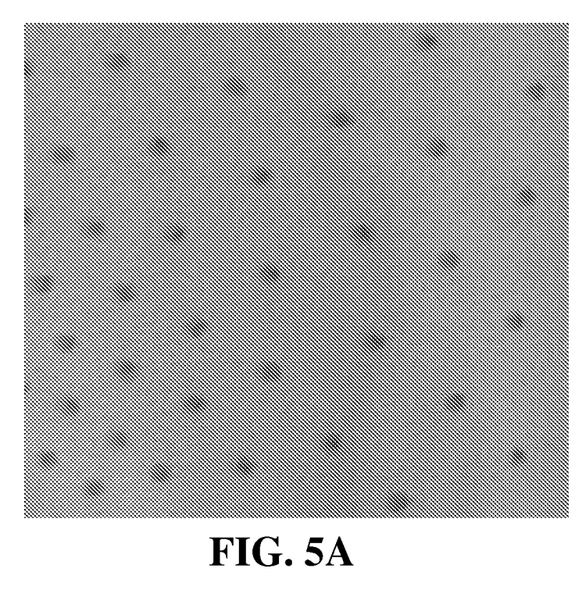
FIGS. 5A and 5B are color photographs of a tissue sheet that has a pH indicator ink deposited topically on the surface of the tissue sheet. The photograph of FIG. 5A shows the tissue before insult and the photograph of FIG. 5B show the tissue after insult with mucus.
Figure 5B:
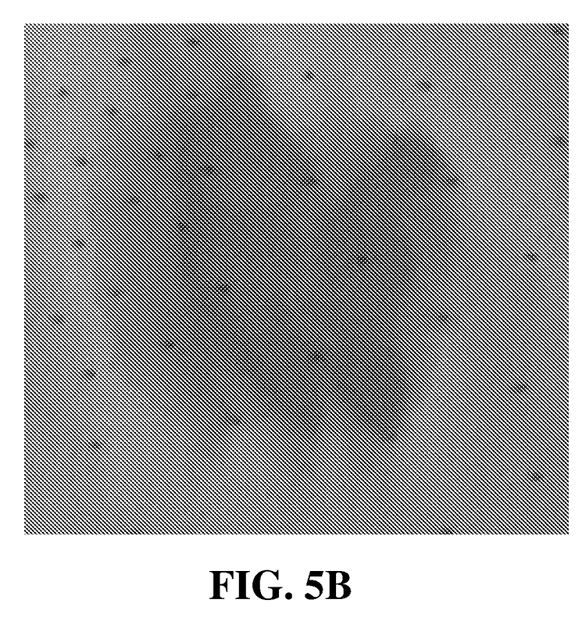

Similar to the preceding examples, a pH indicating ink formulation having: about 0.6 mL Phloxine B (20 mg/mL); 1 mL Benzethonium Chloride (200 mg/mL); 2 mL Organic Varnish; 2 mL Tween 40 (100 mg/mL); 4.4 mL Ethanol is topically applied to the surface of a premade tissue sheet. FIG. 5A shows the tissue before being insulted with mucus, and FIG. 5B shows the same surface after application of the mucus. FIG. 5B shows a change in color from a pale gray or white to a pinkish color.

Example 6

Tissue Sheet with Printed pH Indicator

Figure 6A:
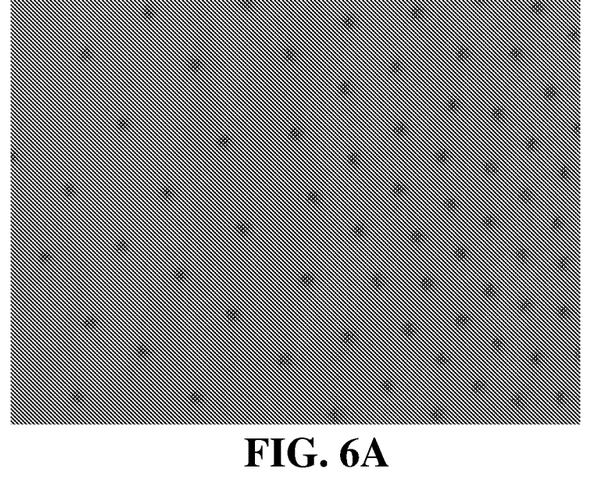
Figure 6B:
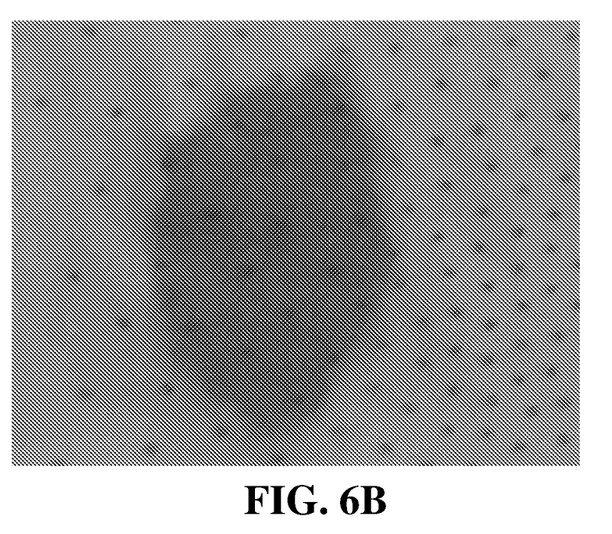

Similar to the preceding Example 5, a pH indicator ink containing: about 0.3 mL Bromocresol Green (20 mg/mL); 1 mL Benzethonium Chloride (200 mg/mL); 2 mL Organic Varnish; 2 mL Tween 40 (100 mg/mL); and 4.7 mL Ethanol is printed on a surface of a premade tissue sheet. FIG. 6A shows a green tissue sheet before insult. FIG. 6B shows the same tissue sheet after insult with mucus. The area of contact with the mucus has turned a blue color.

The present invention has been described in general and in detail in the foregoing examples, which are given for purposes of illustration, and should not to be construed as limiting the scope of this invention, which is defined by the following claims and all equivalents thereto.

We claim:

1. An anti-viral tissue product comprising one or more tissue sheets containing an anti-viral component and a pH indicator, wherein the color of the pH indicator in one or more of the tissue sheets changes when contacted with mucus having a pH of 7.2 to 8.3, wherein the pH indicator is topically applied to one or more of the tissue sheets by means of an ink composition with the following ranges: pH indicator 0.01-10 wt. %; ink carrier medium 20-95 wt. %; surfactant 0-25 wt. %; immobilizer 2-25 wt. %; pH adjuster 0-25 wt. %; and solvent 20-90 wt. %.

2. The product of claim 1, wherein the anti-viral component is acidic.

3. The product of claim 1, wherein the anti-viral component comprises citric acid.

4. The product of claim 1, wherein the color of the pH indicator in one or more of the tissue sheets changes from an initial color to a first color when contacted with mucus having a pH of 7.2 to 8.3 and changes to a second color or reverts to the initial color as the pH of the mucus is changed by the anti-viral component.

5. The product of claim 1, comprising two outer tissue sheets and one or more inner tissue sheets, wherein an inner sheet contains an acidic anti-viral component and the outer sheets contain a pH indicator, wherein the color of the pH indicator in the outer tissue sheets changes when contacted with mucus having a pH of 7.2 to 8.3.

6. The product of claim 1, wherein the pH indicator is 4-anilino-3''-azobenzene, or 4-anilino-3'-azobenzene.

* * * * *